United States Patent
Cavallo et al.

(12) 
(10) Patent No.: US 6,423,749 B1
(45) Date of Patent: Jul. 23, 2002

(54) PHARMACEUTICAL COMPOSITION FOR INJECTION BASED ON PARACETAMOL

(75) Inventors: Giovanni Cavallo, Ostia; Mario Pinza, Corsico, both of (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 09/744,257
(22) PCT Filed: Jul. 27, 1999
(86) PCT No.: PCT/EP99/05486
§ 371 (c)(1),
(2), (4) Date: Jan. 31, 2001
(87) PCT Pub. No.: WO00/07588
PCT Pub. Date: Feb. 17, 2000

(30) Foreign Application Priority Data

Jul. 31, 1998 (IT) .......................................... MI98A1795

(51) Int. Cl.⁷ ............................................... A61K 31/16
(52) U.S. Cl. ...................................................... 514/629
(58) Field of Search ......................................... 514/629

(56) References Cited

U.S. PATENT DOCUMENTS 4,307,073 A    12/1981   Nelson

FOREIGN PATENT DOCUMENTS

WO       WO 9805314      2/1998
WO       WO 98 05314     2/1998
WO       WO 9805314      3/1998

OTHER PUBLICATIONS

Prakongpan et al, Chem. Pharm. ull., 32(1), 340–343, 1984.*

Penin et al;, Rev. Asoc. Esp. Farm. Hosp., 11(4), 249–54, 1987.*

Chemical Abstracts, vol. 109, No. 14, Oct. 3, 1998, Columbus, Ohio, US; abstract No. 115998, XP002125072 abstract & I.R. Penin et al., "Development of Injectable Paracetamol" Rev. Asoc. Esp. Farm. Hosp., vol. 11, No. 4, 1987, pp. 249–254.

Database WPI Week 9444, Derwent Publications Ltd., London, GB; AN 94–355463 '44! XP002097935 abstract & KR 9 311 994 B (Daekwang Pharm. Co.) Dec. 23, 1993.

Database WPI Week 9045, Derwent Publications Ltd. London, GB; AN 90–335491 '45! XP002097936 abstract & DD 279 405 A (Veb Berlin Chemie) Jun. 6, 1990.

Chemical Abstracts, vol. 105, No. 26, Dec. 29, 1986 Columbus, Ohio, US; abstract No. 232386, XP002125073 abstract & Z. Yan et al.: "Preparation of Paracetomal Injections" Yaoxue Tongbao, vol. 21, No. 7, 1986, pp. 387–389.

* cited by examiner

*Primary Examiner*—Rebecca Cook
(74) *Attorney, Agent, or Firm*—Oblon, Spivak, McClelland, Maier & Neustadt, P.C.

(57) ABSTRACT

The invention relates to pharmaceutical compositions comprising paracetamol, ethanol, and polyethylene glycol, either in the absence or the presence of water.

19 Claims, No Drawings

PHARMACEUTICAL COMPOSITION FOR INJECTION BASED ON PARACETAMOL

This is a 371 of PCT/EP99/05486 filed Jul. 27, 1999.

The present invention relates to a pharmaceutical composition for injection based on paracetamol.

In particular, in a first aspect, the present invention relates to a pharmaceutical composition for injection comprising paracetamol, a low molecular weight alcohol and a polyethylene glycol.

It has been known practice for a long time to use paracetamol as an analgesic and an antipyretic.

By virtue of its very satisfactory tolerability, paracetamol is, in some cases, even preferred to NSAIDs (non-steroidal anti-inflammatory drugs) and, in particular, to aspirin. Indeed paracetamol, like aspirin, exhibits its activity by inhibiting the synthesis of the prostaglandins produced by cyclooxygenase. However, unlike most NSAIDs, its inhibition is exerted almost exclusively on the brain and, to a much smaller level, on the peripheral tissues (stomach, kidneys and blood platelets). For this reason its use does not produce the side effects typical of NSAIDs such as, for example, heartburn and gastric lesions with possible loss of blood.

The only possible complication associated with its use is liver cytolysis, although this occurs only in the case of an overdose (Flower R. J., Vane J. R., "Nature", 240, 410–411, 1972; Lanz R., Poster P., "J. Pharmacol", 130, 105–109, 1986,; Black M., "Annual Reviews of Medicine", 35, 577–593, 1984).

It is also known that paracetamol is very slightly soluble in water ("The Merck Index", 12th edition, page 9, No. 45, 1996).

This characteristic represents a major obstacle to its administration by injection. Moreover, in the presence of water, paracetamol undergoes degradations which also give rise to pink- to brown-coloured derivatives. The most common types of degradation are hydrolysis to p-aminophenol and/or oxidation by, for example, oxygen dissolved in water. This second reaction appears to be responsible for the formation of the said derivatives.

Patent application WO 98/05314 attempts to overcome the above-mentioned drawbacks by means of a composition containing a solution of paracetamol in an aqueous solvent in combination with a buffer having a pH of from 4 to 8 and an agent capable of capturing free radicals. In addition, the above-mentioned document recommends removing any oxygen which may be present in the said solvent by means of flushing with a water-insoluble inert gas.

Among the pharmaceutical compositions given as examples in the above-mentioned patent application, those capable of dissolving the majority of paracetamol contain, besides water, PEG-400 and propylene glycol.

In particular, according to the above-mentioned document, a solution consisting of 30% propylene glycol, 40% PEG400 and 30% water is able to dissolve up to about 200 mg/ml of paracetamol at 20° C. (WO 98/05314, page 9, lines 7–12).

However, this solvent mixture is very viscous (see Comparative Example 1) and is thus unsuitable for administration by injection.

There is thus still a great need for a paracetamol-based pharmaceutical composition which, besides containing therapeutic levels of paracetamol, can be injected easily and does not give rise to weals.

It has now been found, surprisingly, that low molecular weight alcohols promote the dissolution of paracetamol in a polyethylene glycol.

As can be seen in the examples, the amount of paracetamol dissolved by a mixture of a low molecular weight alcohol and of a polyethylene glycol (Example 1) is greater than that dissolved, for an equal volume, by the low molecular weight alcohol and polyethylene glycol alone (Comparative Examples 2 and 3).

This is all the more surprising if one considers that, according to the above-mentioned patent application WO 98/05314, the addition of ethanol does not increase the solubility of paracetamol in a polyethylene glycol (page 11, last line).

In a first aspect, the present invention provides a pharmaceutical composition,
a) that comprises
i) paracetamol,
ii) 1 to 4 parts by volume of ethanol for each part by weight of paracetamol, and
iii) 1 to 5 parts by volume of a polyethylene glycol for each part by weight of paracetamol,
b) is substantially anhydrous, and
c) forms a clear solution for injection with 4–10 parts by volume of water for each part by weight of paracetamol.

In a second aspect, the present invention relates to a pharmaceutical composition consisting of a clear solution for injection, comprising paracetamol and, for each part by weight of paracetamol,
i) 1 to 4 parts by volume of ethanol,
ii) 1 to 5 parts by volume of a polyethylene glycol, and
iii) 4 to 10 parts by volume of water, and it does not contain any preserving agents, stabilizers, surfactants, buffers, agents for capturing free radicals, or antioxidants.

Preferably, for each part by weight of paracetamol, the parts by volume of ethanol are between 1.5 and 3, and even more preferably between 2 and 2.5.

In turn, for each part by weight of paracetamol, the parts by volume of polyethylene glycol are preferably between 1.5 and 4. and even more preferably between 2 and 3.

Lastly, the parts by volume of water for each part by weight of paracetamol are preferably between 5 and 8.

Preferably, the polyethylene glycol is chosen from the group comprising PEG-200, PEG-300, PEG-400, PEG-1, 000, PEG-1,540, PEG-4,000 and PEG-8,000.

Typically, the polyethylene glycol is PEG-400.

The organic paracetamol solution according to the first aspect of the present invention is very stable, since the paracetamol does not precipitate out or undergo degradations, even after sterilization at 121° C. for 30 minutes followed by storage at 30° C. under constant illumination at 11,000 lux for at least one month. This stability is found even in the absence of preserving agents, stabilizers, surfactants, buffers, agents for capturing free radicals and/or antioxidants.

By addition of water and simple beating by hand, it then readily forms a clear aqueous solution, in accordance with the second aspect of the present invention.

Typically, the clear aqueous solution for injection thus obtained has a viscosity of between 2 and 10 mPa·s. Preferably, the amount of low molecular weight alcohol, polyethylene glycol and water is adjusted such that the said viscosity is between 4 and 7 mPa·s.

According to another aspect, the present invention thus relates to a clear pharmaceutical solution for injection, characterized in that it comprises ethanol, PEG-400, water and from 10 to 25% (w/v) of paracetamol and in that the amounts of ethanol, of PEG-400 and of water are adjusted such that the viscosity of the said solution is between 4 and 7 mPa·s.

This solution also has the further advantage of not containing any preserving agents, stabilizers, surfactants, buffers, agents for capturing free radicals and/or antioxidants.

The pharmaceutical composition of the present invention can be prepared according to techniques that are well known in pharmaceutical chemistry, comprising mixing, dissolution, sterilization and the like.

The present invention will be further described by the following examples, which are given for purely illustrative purposes and should not be interpreted in a limiting sense.

EXAMPLE 1

Organic paracetamol solutions
Solution A

| Component | Amount |
| --- | --- |
| Paracetamol | 50 g |
| Absolute ethanol | 100 ml |
| PEG-400 | 100 ml |

The absolute ethanol and the PEG-400 were added to the paracetamol at room temperature. This mixture was then stirred until the paracetamol had completely dissolved (about 30 minutes).

Some of the solution thus obtained was divided between 60 5-ml bottles in a proportion of 3 ml per bottle.

On some samples, freshly prepared (time 0), the following controls were carried out:

paracetamol titre: HPLC (mg/ml)

p-aminophenol titre: HPLC (mg/ml) and check for any coloured degradation products: spectrophotometry at 475 nm and the following results were obtained:

average paracetamol titre: 214.1 p-aminophenol: absent average absorption: 0.0075

The above-mentioned samples were then stored for one month under the following conditions:

at 4° C. (Samples A), at room temperature (Samples B)

at 30° C. in a room under an illumination of 11,000 lux (Samples C).

The results obtained are given in Table 1 below.

TABLE 1

| Sample | Paracetamol titre (mg/ml) | p-aminophenol titre (mg/ml) | Absorption 475 nm |
| --- | --- | --- | --- |
| A | 213.0 | absent | 0.0083 |
| B | 218.0 | absent | 0.0082 |
| C | 217.0 | absent | 0.0250 |

Other samples (Samples D), freshly prepared (time 0), showed the following characteristics:

paracetamol titre: 204.0 p-aminophenol: absent absorption: 0.0062

They were stored for one month at 30° C. in a room under an illumination of 11,000 lux and showed the following characteristics:

paracetamol titre: 203.0 p-aminophenol: absent absorption: 0.0162

Lastly, another group of samples (Samples E), freshly prepared (time 0) and after sterilization (121° C. for 30 minutes), showed the following characteristics:

paracetamol titre: 202.8 p-aminophenol: absent absorption 0.0100

They were stored for one month at 30° C. in a room under an illumination of 11,000 lux and showed the following characteristics:

paracetamol titre: 202.0 p-aminophenol: absent absorption: 0.0104

Solutions B and C

Similar results were obtained with samples having the following compositions.

| Component | Amount |
| --- | --- |
| Solution B | |
| Paracetamol | 50 g |
| Absolute ethanol | 100 ml |
| PEG-400 | 150 ml |
| Solution C | |
| Paracetamol | 80 g |
| Absolute ethanol | 200 ml |
| PEG-400 | 200 ml |

EXAMPLE 2

Aqueous Solution for Injection

Solution A (8 ml), prepared as described in Example 1 above, was introduced into a bottle (20 ml). Distilled water for injection (12 ml) was added. The bottle was then shaken manually until a clear solution was obtained (about 10–40 seconds).

The solution thus obtained showed the following physicochemical characteristics:

Appearance: clear, colourless

Viscosity*: 5.068 mPa·s

Osmolarity calculated: 529.2 mOsmol/litre

Density**: 1.02600 g/cm$^3$

*measured with a Carri-Med CSL 50 Rheometer viscosimeter;

**measured with a Mettler Toledo DA-310 M densitometer.

COMPARATIVE EXAMPLE 1

Aqueous solution for Injection according to patent application WO 98/05314

| Component | Amount |
| --- | --- |
| Paracetamol | 1,600 mg |
| Propylene glycol | 2.7 ml |
| PEG-400 | 3.6 ml |
| Sodium acetate | 20 mg |

-continued

| Aqueous solution for Injection according to patent application WO 98/05314 | |
|---|---|
| Component | Amount |
| Reduced glutathione | 20 mg |
| Hydrochloric acid | qs pH 6 |

The above-mentioned composition, prepared as described in patent application WO 98/05314, was introduced into a 15-ml bottle. Distilled water for injections (3.7 ml) was added thereto and the mixture was left stirring until a clear solution was obtained (30 minutes).

The solution thus obtained showed the following physicochemical characteristics:

Appearance: clear, colourless
Viscosity*: 37.40 mPa·s
Osmolarity calculated: 1,088.8 mOsmol/litre
Density**: 1.09685 g/cm$^3$ By working in a similar manner to that described above, a second composition was prepared containing 800 mg of paracetamol instead of 1.600 mg.

This solution showed the following physicochemical characteristics:

Appearance: clear, colourless
Viscosity*: 26.34 mPa·s
Osmolarity calculated: 560 mOsmol/litre
Density**: 1.09433 g/cm$^3$

COMPARATIVE EXAMPLE 2

| Alcohol-free organic paracetamol solution | |
|---|---|
| Component | Amount |
| Paracetamol | 5 g |
| PEG-400 | 10 ml |

The PEG400 was added to the paracetamol at room temperature. This mixture was then kept stirring at room temperature for 2 hours.

4 ml of the above-mentioned suspension were centrifuged in an Eppendorf tube at 25° C. for 30 minutes at a speed of 7,000 rpm.

HPLC analysis of the supernatant thus obtained showed that the solubility of the paracetamol was 18–19%.

COMPARATIVE EXAMPLE 3

| PEG-free organic paracetamol solution | |
|---|---|
| Component | Amount |
| Paracetamol | 5 g |
| Absolute ethanol | 10 ml |

The absolute ethanol was added to the paracetamol at room temperature. This mixture was then kept stirring at room temperature for 2 hours.

4 ml of the above-mentioned suspension were centrifuged in an Eppendorf tube at 4° C. for 40 minutes at a speed of 7,000 rpm.

HPLC analysis of the supernatant thus obtained showed that the solubility of the paracetamol was 9–10%.

What is claimed is:

1. A pharmaceutical composition, comprising
    i) paracetamol,
    ii) 1 to 4 parts by volume of ethanol for each part by weight of paracetamol, and
    iii) 1 to 5 parts by volume of a polyethylene glycol for each part by weight of paracetamol,
        wherein said composition,is substantially anhydrous.
2. The pharmaceutical composition according to claim 1, comprising 1.5 to 3 parts by volume of ethanol for each part by weight of paracetamol.
3. The pharmaceutical composition according to claim 2, comprising 2 to 2.5 parts by volume of ethanol for each part by weight of paracetamol.
4. The pharmaceutical composition according to claim 1, comprising 1.5 to 4 parts by volume of polyethylene glycol for each part by weight of paracetamol.
5. The pharmaceutical composition according to claim 4, comprising 2 to 3 parts by volume of polyethylene glycol for each part by weight of paracetamol.
6. The pharmaceutical composition according to claim 1, wherein the polyethylene glycol is selected from the group consisting of PEG-200, PEG-300, PEG-400, PEG-1,000, PEG-1,540, PEG-4,000 and PEG-8,000.
7. The pharmaceutical composition according to claim 6, wherein the polyethylene glycol is PEG-400.
8. The pharmaceutical composition of claim 1, wherein said composition forms a clear solution for injection with the addition of 4–10 parts by volume of water for each part by weight of paracetamol.
9. The pharmaceutical composition according to claim 8, comprising 5 to 8 parts by volume of water for each part by weight of paracetamol.
10. A clear pharmaceutical composition for injection, comprising paracetamol and, for each part by weight of paracetamol,
    i) 1 to 4 parts by volume of ethanol,
    ii) 1 to 5 parts by volume of a polyethylene glycol, and
    iii) 4 to 10 parts by volume of water, and it does not contain any preserving agents, stabilizers, surfactants, buffers, agent for capturing free radicals, or antioxidants.
11. The pharmaceutical composition according to claim 10, comprising 1.5 to 3 parts by volume of ethanol for each part by weight of paracetamol.
12. The pharmaceutical composition according to claim 10, comprising 2 to 2.5 parts by volume of ethanol for each part by weight of paracetamol.
13. The pharmaceutical composition according to claim 10, comprising 1.5 to 4 parts by volume of polyethylene glycol for each part by weight of paracetamol.
14. The pharmaceutical composition according to claim 10, comprising 2 to 3 parts by volume of polyethylene glycol for each part by weight of paracetamol.
15. The pharmaceutical composition according to claim 10, wherein the polyethylene glycol is selected from the group consisting of PEG-200, PEG-300, PEG-400, PEG-1,000, PEG-1,540, PEG-4,000 and PEG-8,000.
16. The pharmaceutical composition according to claim 15, wherein the polyethylene glycol is PEG-400.
17. A clear pharmaceutical solution for injection, comprising ethanol, PEG-400, water and from 10 to 25% (w/v) of paracetamol, wherein the amounts of ethanol, of PEG-400 and of water are adjusted such that the viscosity of the said solution is between 4 and 7 mPa·s.

18. A method of making a pharmaceutical composition, comprising mixing paracetamol, 1 to 4 parts by volume of ethanol for each part by weight of paracetamol, and 1 to 5 parts by volume of a polyethylene glycol for each part by weight of paracetamol.

19. A method of making a pharmaceutical composition, comprising mixing paracetamol, 1 to 4 parts by volume of ethanol for each part by weight of paracetamol, 1 to 5 parts by volume of a polyethylene glycol for each part by weight of paracetamol, and 4 to 10 parts by volume of water.

* * * * *